US00PP13454P3

(12) United States Plant Patent

Olesen et al.

(10) Patent No.: US PP13,454 P3

(45) Date of Patent: Jan. 7, 2003

(54) MINIATURE ROSE PLANT NAMED 'POULRA004'

(76) Inventors: L. Pernille Olesen, Hillerødvejen 49, DK-3480, Fredensborg (DK); Mogens N. Olesen, Hillerødvejen 49, DK-3480, Fredensborg (DK)

( * ) Notice: Subject to any disclaimer, the term of this patent is extended or adjusted under 35 U.S.C. 154(b) by 25 days.

(21) Appl. No.: 09/774,293

(22) Filed: Jan. 29, 2001

(65) Prior Publication Data

US 2001/0020301 P1 Sep. 6, 2001

(51) Int. Cl.[7] ..... A01H 5/00

(52) U.S. Cl. ..... Plt./116

(58) Field of Search ..... Plt./116, 120, 121, Plt./128, 123

*Primary Examiner*—Bruce R. Campell
*Assistant Examiner*—June Hwu

(57) ABSTRACT

A new miniature rose plant which has abundant, pink flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

SUMMARY OF THE INVENTION

Botanical: *Rosa hybrida* 'POULra004'.
Commerical: Miniature.

The present invention constitutes a new and distinct variety of miniature rose plant which originated from a controlled crossing between 'KORstoffein', described and illustrated in U.S. Plant Pat. No. 11,242, dated Feb. 22, 2000 and an 'unnamed seedling'. The two parents were crossed and the resulting seeds were planted in a controlled environment. The new variety is named 'POULra004'.

The new rose may be distinguished from its seed parent, 'KORstoffein', by the following combination of characteristics:

1. The flower color of the seed parent is a paler pink than 'POULra004'.
2. The duration of blooms on 'POULra004' is greater.

The new variety may be distinguished from its pollen parent, an 'unnamed seedling' created by the same inventors, by the following combination of characteristics:

1. Pollen parent has yellow flowers.
2. Pollen parent growth is more vigorous.
3. Pollen parent habit is more spreading than 'POULra004'.

The objective of the hybridization of this rose variety for commercial culture was to create a new and distinct variety with unique qualities, such as:

1. Uniform and abundant pink flowers;
2. Vigorous and compact growth;
3. Year-round flowering under glasshouse conditions;
4. Suitability for production from softwood cuttings in pots;
5. Durable pink flowers and foliage which make a variety suitable for distribution in the floral industry.

This combination of qualities is not present in previously available commercial cultivars of this type and distinguich 'POULra004' from all other varieties of which we are aware.

As part of their rose development program, L. Pernille Olesen and Mogens N. Olesen germinated the seeds from the aforementioned hybridization and conducted evaluations on the resulting seedlings in a controlled environment in Fredensberg, Denmark.

'POULra004' was selected by the inventors as a single plant from the progeny of the hybridizaton in Spring 1999.

Asexual reproduction of 'Poulra004' by cuttings was first done by L. Pernille and Mogens N. Olesen in their nursery in Fredensborg, Denmark in June 1999. This initial and other subsequent propagations conducted in controlled environments have demonstrated that the characteristics of 'POULra004' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'POULra004'. Specifically illustrated in Sheet 1:

1. Stem showing branching and the attachment of leaves, buds, and peduncles;

2. Flower bud, partially opened bud, and open bloom;

3. Flower petals, detached;

4. Sepals receptacle, and peduncle;

5. Flowering stem as well as a bare stem exhibiting thorns;

6. Leaves.

DETAILED DESCRIPTION OF THE VARIETY

The following is a description of 'POULra004', as observed in its growth in Burlington, Ontario, Canada, on plants aged 15 weeks. Color references are made using The Royal Horticultural Society (London, England) Colour Chart, 1995, except where common terms of color are used.

For a comparison, several physical characteristics of the rose variety 'POULcar', a rose variety from the same inventors described and illustrated in U.S. Plant Pat. No. 7,999 and issued on Oct. 13, 1992 are compared to 'POULra004' in Chart 1.

CHART 1

| | 'POULra004' | 'POULcar' |
|---|---|---|
| Color - upper side of petal, after opening. | Red Group 56D | Red Group 38C |
| Bloom size | 45–50 mm | 33–35 mm |
| Number of petals | 40–50 | 60 |

Parents: 'KORstoffein'×'unnamed seedling'.

FLOWER AND FLOWER BUD

Blooming habit: Continuous.

Flower bud:

*Size.*—Upon opening, 25 mm in length from base of receptacle to end of bud.

*Bud form.*—Short and globular.

*Bud color.*—As sepals unfold, Red Group 38B with guard petals having an intonations of Yellow-Green 145B–C. Red Group 38B at ¼ opening.

*Sepals.*—Green Group 146B. Medium foliaceous appendages on 3 of the 5 sepals. Surfaces of sepals moderately pubescent. Stipitate glands are present on sepal margins and on outer surface of the sepal. Sepals are 40 mm long and 10 mm wide.

*Anthocyanin.*—On sepals of juvenile buds. Color: Greyed-Red Group 181B–C.

*Receptacle.*—Surface: Smooth. Shape: Urn-shaped. Size: Small. 10 mm (h)×8 mm (w). Color: Yellow-Green Group 146D.

*Peduncle.*—Surface: Moderate number of stipitate glands present. Length: 24–28 mm average length. Color: Yelow-Green Group 146C. On plants grown under high light conditions, peduncle may exhibit intonations of Greyed-Red Group 181B–C. Strength: Strong.

*Borne.*—Typically borne one bud per flowering stem, less commonly 2–3 buds per flowering stem.

Flower bloom:

*Fragrance.*—Light.

*Duration.*—As a pot plant, flowers last from 18 to 22 days. As a cut flower 6 to 8 days. The blooms have a duration on the plant of approximately 10 to 12 days. Petals are not self-cleaning.

*Size.*—Large for an 8–11 cm pot rose. Average flower diameter is 45–50 mm when open.

*Form.*—Shape of flower when viewed from the side: Upon opening, upper part: Flat. Upon opening, lower part: Convex. Open flower, upper part: Flat. Open flower, lower part: Flattened convex.

*Petalage.*—Very double. Average range: 40–50 petals under normal conditions with 5–15 petaloids.

Color:

*Upon opening, petals.*—Outermost petals: Outer Side: Red Group 38B. Inner Side: Red Group 38C. Innermost petals: Outer Side: Orange-Red Group 31D. Inner Side: Yellow-Orange Group 22C.

*Upon opening, basal petal spots.*—Outermost petals: Outer Side: Yellow-Green Group 149B. Inner Side: Green-Yellow Group 1C. Innermost petals: Outer Side: Yellow Group 3B. Inner Side: Yellow Group 3A.

*After opening, petals.*—Outermost petals: Outer Side: Red Group 56D. Inner Side: Red Group 56D. With intonations of Yellow-Green Group 145C emanating from the basal petal spot well into the middle zone of petal. Innermost petals: Upper Side: Orange Group 27B. Inner Side: Orange Group 29C.

*After opening, basal petal spots.*—Outermost petals: Outer Side: Yellow-Green Group 150B. Inner Side: Yellow Group 5B. Innermost petals: Outer Side: Yellow Group 4A. Inner Side: Yelow Group 3A.

General tonality: Blend of colors on open flower. Outer edge of flower Red Group 36B, with center of flower Orange Group 24D. No change in the general tonality at the end of the $14^{th}$ day. Afterwards, general tonality is Orange Group 22C with outer portion of flower Yellow-Orange 20C.

Petals:

*Petal reflex.*—Strongly reflexed.

*Petal edge.*—Entire.

*Shape.*—Deltoid. Apex is mucronate.

*Petaloids.*—Present. Quantity: 5–15. Color: Orange Group 27B. Size: 7 mm wide and 10 mm long. Texture is smooth.

*Thickness.*—Thin.

*Arrangement.*—Imbricated.

*Size.*—20 mm wide and 20 to 25 mm long.

*Texture.*—Smooth.

Reproductive organs:

*Pollen.*—Color: Yellow-Orange Group 20A. Quantity: Average.

*Anthers.*—Size: 2 mm long. Color: Yellow Group 3D. Quantity: 25 to 30.

*Filaments.*—Color: Yellow Group 13B. Length: 8 mm.

*Stigma.*—Superior in position to the anthers. Color: Greyed-Yellow Group 160C.

*Styles.*—Color: Greyed-Green Group 196C. Length: 6 mm. Quantity: 25 to 30.

*Seed formation.*—Hips not observed.

PLANT

Plant growth: Vigorous, compact, and upright. When grown as an 8–11 cm pot plant, the average height of the plant is 18–20 cm and the average width is 17–19 cm. When grown as a nursery plant on its own roots the average plant height is 25–30 cm and the average plant width is 25–35 cm.

Stems:

*Color.*—Young wood: Yellow-Green Group 144A. Older wood: Yellow-Green Group 144B.

*Prickles.*—Incidence: Moderate. Size: Average length: 3–5 mm. Color: Base: Green-White Group 157B. Tip: Greyed-Red 181A. Shape: Deeply concave.

*Surface.*—Young wood: Smooth. Older wood: Smooth.

Plant foliage: Typical number of leaflets on normal leaves in middle of the stem: 5 to 7 leaflets.

*Typical leaf size.*—Small, 60–70 mm (l)×40–50 mm (w).

*Abundance.*—Average.

*Color.*—Mature Leaves: Upper Leaf Surface: Green Group 137A. Lower Leaf Surface: Yellow-Green Group 147B. Juvenile foliage: Upper Surface: Yellow-Green Group 146A. Lower Surface: Green Group 137C. Anthocyanin: Anthocyanin intonations of Greyed-Red 181B–C present on lower side of mature and immature foliage.

Plant leaves and leaflets:

*Stipules.*—Size: 8 mm (l)×3 mm (w). Color: Yellow-Green Group 146B. Anthocyanin: Inotonations of Greyed-Red Group 181B–C located along the margins of immature foliage. Presence of stipitale glands: Numerous present along margins.

*Petiole.*—Length: 10–12 mm. Color: Yellow-Green Group 146C. Underneath: Small prickles. Margins: Numerous stipitate glands. Anthocyanin: Along margins of juvenile and mature foliage. Color: Greyed-Red Group 181B.

*Rachis.*—Color: Yellow-Green Group 146D. Underneath: Small prickles and a few stipitate glands. Margins: Stipitate glands present. Anthocyanin: Lower surface of juvenile foliage. Color: Greyed-Red Group 181B.

*Leaflet.*—Edge: Finely serrated. Shape: Ovate. Surface texture: Moderately glossy and thin.

Disease resistance: Above average resistance to mildew, black spot, and Botrytis under normal growing conditions in Jackson County, Oreg.

Cold Hardiness: The variety 'POULra004' has been found to be resistant to damage from cold in USDA Zone 7.

We claim:

1. A new and distinct variety of rose plant of the miniature class, substantially as herein illustrated and described as a distinct and novel rose variety due to its abundant, pink flowers, vigorous growth, compact habit, suitability for production from softwood cuttings in pots, and durable flowers and foliage which make the variety suitable for distribution in the floral industry.

* * * * *

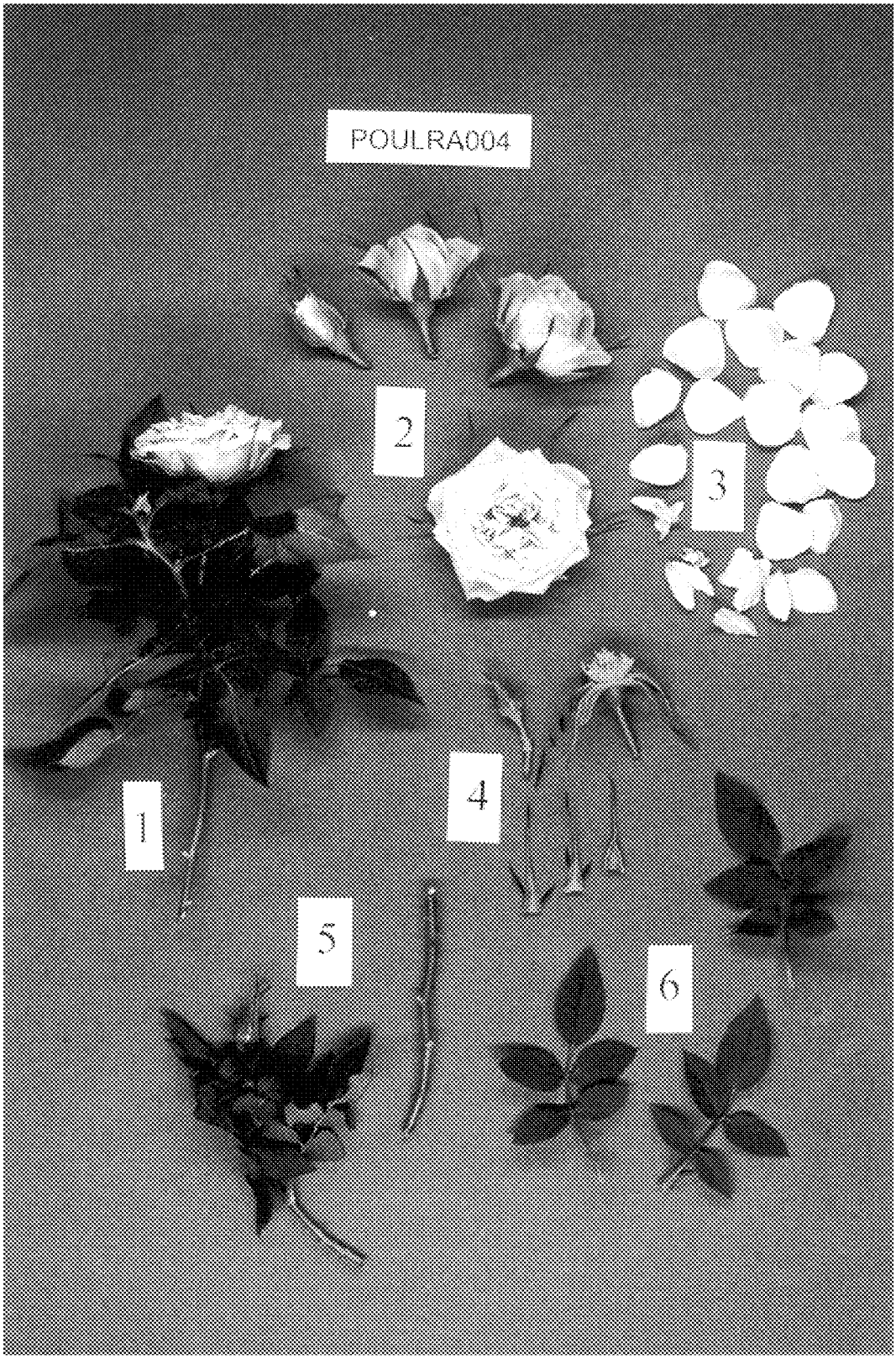
POULRA004
1
2
3
4
5
6